United States Patent
Moy

(10) Patent No.: US 9,585,962 B1
(45) Date of Patent: Mar. 7, 2017

(54) TREATMENT FOR ACTINIC KERATOSES

(71) Applicant: Lawrence Moy, Manhattan Beach, CA (US)

(72) Inventor: Lawrence Moy, Manhattan Beach, CA (US)

(*) Notice: Subject to any disclaimer, the term of this patent is extended or adjusted under 35 U.S.C. 154(b) by 0 days.

(21) Appl. No.: 14/585,760

(22) Filed: Dec. 30, 2014

Related U.S. Application Data

(60) Provisional application No. 61/922,047, filed on Dec. 30, 2013.

(51) Int. Cl.
- *A61K 31/165* (2006.01)
- *A61K 47/40* (2006.01)
- *A61K 9/00* (2006.01)
- *A61K 9/06* (2006.01)

(52) U.S. Cl.
CPC ............ *A61K 47/40* (2013.01); *A61K 9/0014* (2013.01); *A61K 9/06* (2013.01); *A61K 31/165* (2013.01)

(58) Field of Classification Search
CPC ...................................................... A61K 47/40
USPC ........................................................ 514/629
See application file for complete search history.

(56) References Cited

PUBLICATIONS

Kurkov et al., Int. J. Pharmaceutics, vol. 453 (2013), pp. 167-180 (published online Jul. 5, 2012).*

* cited by examiner

*Primary Examiner* — Taofiq A Solola
(74) *Attorney, Agent, or Firm* — Zuber Lawler & Del Duca LLP; Stefan J. Kirchanski; Matthew J. Spark

(57) ABSTRACT

A composition of cyclodextrin and colchicine in a dermatologically acceptable cream base provided improved clearance of actinic keratoses following topical application for 1 to 3 months. The composition provides improved clearance of recalcitrant actinic keratoses. Furthermore, the treatment causes much less pain and irritation than other topical treatments for actinic keratoses.

6 Claims, No Drawings

TREATMENT FOR ACTINIC KERATOSES

This application claims priority to U.S. Provisional Patent Application No. 61/922,047 to Moy, filed Dec. 30, 2013 entitled "New Treatments for Actinic Keratoses," the subject matter of which is being incorporated herein by reference in its entirety.

AREA OF THE ART

The present invention is in the art of dermatology and more specifically relates to a topical composition for the treatment of actinic keratoses.

DESCRIPTION OF THE BACKGROUND OF THE INVENTION

Although some exposure to sun light is critical to the synthesis of Vitamin D, sun light is not harmless. Absorption of infrared light results in heating of the skin and can potentially damage tissues through a "cooking-like" phenomenon. Absorption of visible and ultraviolet light also causes heating, but these wavelengths are much more energetic. Ultraviolet light, and to a lesser extent visible light, are sufficiently energetic to result in chemical changes. The tanning response is largely the skin's attempt to protect itself by providing a shading barrier to sunlight.

Although light can induce chemical changes (i.e., damage) to a large variety of biological structures, probably the most significant damage is caused by the ability of ultraviolet light to induce photochemical changes in the pyrimidine bases of DNA (deoxyribonucleic acid). A common expression of this photochemistry is the dimerization of the thymine bases. Such dimerization affects the replication and translation of the genetic material. Cells contain repair mechanisms to excise and replace the damaged regions of DNA, but these mechanisms are not one hundred percent accurate. Therefore, ultraviolet damage introduces mutations into the DNA which can result in abnormal cell growth including precancerous and cancerous lesions.

A common ultraviolet induced lesion occurs when the genetic material of the keratinocytes becomes damaged. Specifically, DNA alterations of keratinocytes in the basal layer of the epidermis result in Actinic Keratoses (AKs). The AKs are crusty, thick, scaly and/or often pigmented premalignant (precancerous) lesions. When abnormal cells spread to or occur in the dermis, the lesion is defined as a squamous cell carcinoma, and the lesion has converted into a true skin cancer. Because a significant number of AKs progress to squamous cell carcinoma, it is important to treat (i.e., remove) AKs. The treatment of AKs is very common in dermatology particularly in sunny regions. Increased sun activities over a lifetime increase the risk for these AK's. In Southern California, AKs are very prevalent in the population from the age of 30 years to the elderly.

At the present time, the conventional treatment for AKs is to spray or apply cryogenic liquid nitrogen ($LN_2$) to the lesions. This treatment generally works well for discrete specific lesions; however, the skin can experience sufficient sun damage that AKs will keep appearing even with regular liquid nitrogen treatment. There are some creams that can treat incipient AKs and/or AKs that that are already present.

The most common creams contain 5-fluorouracil (5% is the most popular concentration), which is actually an artificial analog of the DNA base thymidine. It is known as a "suicide inhibitor" because it irreversibly blocks the enzyme thymidylate synthase. Blocking the synthase results in a shortage of thymidine which blocks DNA replication in rapidly growing cancer and precancerous cells thereby resulting in cell death. The reaction to this treatment (which is typically 4-6 weeks in duration) is crusted, very painful, very red lesions and peeling of the skin. Even when the 5-fluorouracil treatment is effective, AKs often return and the patient still needs to be followed to watch for further development of AKs. In the inventor's more than 25 years of practicing dermatology, his patients have reported some ultimately positive results from the 5-fluorouracil creams, but most patients would choose not to go through the 4-6 weeks of discomfort and unsightly appearance that results from the treatment. Patients have a very difficult time with this treatment if they need to be seen in public for employment purposes or at any social occasion. Many patients who have received 5-fluorouracil treatments regret having taken those treatments because of the side effects.

All current AK treatments have significant drawbacks. Liquid nitrogen ($LN_2$) treatments require regular freezing to the affected areas for adequate control of AKs. $LN_2$ is a common treatment that can be effective in some cases. However, with an increased number of lesions on the face, $LN_2$ treatment can become very traumatic. The freezing hurts and causes scabbing, crusting, blistering and pain for 7-10 days. In addition, it can result in scarring. In some cases, depending on how much sun damage has accumulated over the years or depending on the ongoing sun damage the patient is still receiving (e.g. lifeguards), $LN_2$ treatment is not effective. Furthermore for other body areas, including the scalp or the arms and legs, $LN_2$ treatment is less effective.

Furthermore, some patients without obvious onset of squamous cell carcinoma (SCC) or basal cell carcinoma (BCC) show conversion of the AKs to SCC or BCC. With an excessive amount of chronic sun exposure, there is an increase of progression of AKs to skin carcinomas. Clearly alternate treatments for AKs beyond $LN_2$ and 5-fluorouracil are sorely needed.

SUMMARY OF THE INVENTION

Colchicine is one drug that has been used in the past to treat AKs. Colchicine prevents cell division by binding to microtubule proteins. However, colchicine fell out of favor because at concentrations sufficient to effectively treat AKs, significant skin irritation resulted. The inventor has experimented with a number of different formulations in an attempt to enhance colchicine effectiveness while reducing colchicine-induced irritation. It has been discovered that combining colchicine with cyclodextrin in a cream base results in improved effectiveness against AKs without as much irritation. Optimally, the colchicine is combined with the cyclodextrin on at least an equimolar basis although an excess of cyclodextrin is preferred. An optimal formulation contains about 0.3% by weight colchicine combined with about 1.0% by weight 11 cyclodextrin which represents an approximately three fold excess of cyclodextrin over colchicine. This formulation causes an effective clearing of AKs in a majority of difficult patients with little scarring or discomfort.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a novel topical composition for the improved treatment of actinic keratoses.

The present inventor has experimented with AK cures for some time. Earlier he discovered that colchicine, a historical treatment for AKs, could be combined with gentamicin. Although colchicine alone can be a somewhat effective treatment for AKs, it has significant drawbacks. With colchicine alone (0.1% in a dermatologically acceptable cream base) treatment, it was found that approximately 35-40% of the actinic keratoses were cleared in the patients tested. Unfortunately, this treatment showed a significant level of skin irritation. Skin irritation is likely the reason that colchicine is not commonly used in present day dermatologic treatments. Since a goal of the present invention is to reduce skin irritation, colchicine alone was not adequate.

When combined with gentamicin (0.3% gentamicin+ 0.2% colchicine) the results were superior to 0.1% colchicine with lower levels of irritation. Now the inventor has discovered a colchicine formula that is even more effective. Presented here a controlled, double-blind study of the new formula and shows it to be effective on actinic keratosis without a significant skin reaction.

The major active ingredient of the composition is colchicine in a dermatologically acceptable cream base. The cream base is an oil-in-water emulsion of lipophilic components including caprylic/capric triglycerides, stearyl alcohol, stearic acid and diisopropyl dimer dilinoleate with glyceryl monostearate, PEG-100 Stearate and PEG-40 Stearate as emulsifiers. Propylene glycol is included as a cosolvent. Aluminum magnesium silicate and silica gel are used as thickening, opacifying agents. Trace amounts of methylparaben, propylparaben, imidazolidinyl urea, propyl gallate and BHA (butylated hydroxyanisole) are added as antioxidants and preservatives. Citric acid is used as a pH adjustor and preservative.

Specifically, the cream base formula is:

| Ingredient | Percent |
|---|---|
| water | 76.75% |
| caprylic/capric triglycerides | 9.2% |
| stearyl alcohol | 1.5% |
| stearic acid | 1.5% |
| diisopropyl dimer | 2% |
| polyoyxethylene stearate | 1.1% |
| magnesium aluminum silicate | 1.1% |
| glyceryl stearate/PEG 100 Stearate | 1.5% |
| propylene glycol | 4% |
| silica gel | 0.2% |
| BHA/BHT/Citric Acid/Propyl gallate | 0.15% |
| methylparaben/propylparaben/imidazolidinyl urea | 1% |

It is to be understood that the precise composition of the cream base is not critical and can be altered considerably without changing efficacy.

Colchicine.

Colchicine is an alkaloid that binds to tubulin (the protein makes up microtubules). This binding blocks the polymerization of tubulin into microtubules and inhibits mitosis (cell division) because mitosis is dependent on microtubules to form the spindle, a structure that distributes the chromosomes during cell division. Thus, colchicine can block cell division. For this reason colchicine continues to be investigated as an anticancer drug. At one time colchicine was used as a treatment for skin cancers and precancerous lesions (AKs) of the skin, and colchicine has been studied in the medical literature for AKs over the years, although in the last 17-20 years, there has not been a study that actually used the ingredient.

The major problem with colchicine is that it's effectiveness at a level of 0.1% is not particularly high while at the same time being quite irritating. Attempts to increase effectiveness of the product by increasing the concentration of colchicine merely increases the irritation produced. I reasoned that a complexing agent could increase the effectiveness of delivery. I was surprised and delighted to discover that addition of 11 cyclodextrin (1.0%) to the cream base allowed the use of a higher concentration of colchicine (0.3%) while essentially eliminating the resulting irritation. Cyclodextrins are amylose ($\alpha$ 1,4 glucose polymer) rings containing usually 6-8 glucose units. The interior of the ring is hydrophobic while the exterior of the ring is hydrophilic. This allows cyclodextrins to complex or sequester hydrophobic molecules. It seems likely that the cyclodextrin molecules sequester the colchicine thereby preventing certain cytotoxic responses which lead to irritation while actually potentiating cell death of the most damaged AK cells. I have not yet completed experiments with other common cyclodextrins (a and γcyclodextrins). Since 11 cyclodextrin is soluble to only about 1.8%, it may be that the other cyclodextrins can advantageously be used at higher concentrations than is possible with 11 cyclodextrin. In the current formulation there is approximately three cyclodextrin molecules per colchicine molecule.

Method.

Patients with current AK lesions were evaluated to participate in the study. Patients had been treated previously for AKs, mostly with conventional liquid nitrogen application. Patients were given a rest period of three months without treatment before entering the study. The study was double blinded for half-face applications. The study was designed with two creams, a Control Cream that contained the exact formulation of the other cream and the Active Cream that contained the cream formulation with the active ingredients (cyclodextrin+colchicine). The investigational nurse randomly determined which half-face the patient applied the control cream and to which half-face the patient applied the active cream.

Patients were instructed to apply the cream once a day, usually in the evening. The patients applied the product for six weeks. The application was to the local areas where the AKs tended to recur. Evaluations were performed by a dermatologist who was blinded as to which cream was applied to which half-face. Results are shown in the following table.

|  | Sex | Control: % Cleared | Active: % Cleared |
|---|---|---|---|
| RS | M | 10 | 100 |
| LK | M | 0 | 72 |
| TM | F | 21 | 80 |
| GC | F | 10 | 40 |
| CM | F | 7 | 35 |
| EW | M | 5 | 45 |
| WG | M | 0 | 56 |
| DG | F | 0 | 74 |
| NM | M | 25 | 67 |
| CS | M | 20 | 85 |
| AS | M | 14 | 57 |
| CG | F | 0 | 50 |
| JW | M | 8 | 62 |

-continued

|   | Sex | Control: % Cleared | Active: % Cleared |
|---|---|---|---|
| SK | M | 4 | 37 |
| DH | M | 10 | 40 |
| Average |   | 9 | 60 |

Both creams were well tolerated. Reactions were minimal with both creams. Patients responded well to the Active Cream. It was effective; statistical differences were very clear between the Active Cream and Control Cream. Most significantly, the crusting, erythema, pain, and itching of typical or prior art actinic keratosis creams do not occur with the Active Cream.

The addition of cyclodextrin to the colchicine results in a dramatic reduction in the irritation caused by colchicine. Since colchicine's propensity for causing skin irritation prevented the test of 0.3% colchicine alone, it is not known is the increased efficacy is due entirely to the higher concentration of colchicine or to an interaction between cyclodextrin and colchicine. It seems likely that the concentration of both agents can be further optimized. A still higher level of colchicine may be even more effective. It might be necessary to increase the concentration of cyclodextrin to ensure minimal irritation under those conditions.

The following claims are to be understood to include what is specifically illustrated and described above, what is conceptually equivalent, what can be obviously substituted and also what incorporates the essential idea of the invention.

The illustrated embodiment has been set forth only for the purposes of example and that should not be taken as limiting the invention. Those skilled in the art will appreciate that various adaptations and modifications of the just-described preferred embodiment can be configured without departing from the scope of the invention. Therefore, it is to be understood that, within the scope of the appended claims, the invention may be practiced other than as specifically described herein.

What is claimed is:

1. A method for reducing skin irritation during treatment of actinic keratoses comprising the step of periodically topically applying a mixture of about 0.3% by weight colchicine and cyclodextrin in a pharmaceutically acceptable cream base composition to actinic keratoses.

2. The method according to claim 1, wherein the molar concentration of colchicine to cyclodextrin is about one to three.

3. The method according to claim 1, wherein the cyclodextrin is β cyclodextrin.

4. A composition for reduction of irritation during the topical treatment of actinic keratoses comprising cyclodextrin and about 0.3% by weight colchicine in a pharmaceutically acceptable cream base composition.

5. The composition according to claim 4, wherein the molar concentration of colchicine and cyclodextrin are about equal.

6. The composition according to claim 4, wherein the cyclodextrin is β cyclodextrin.

* * * * *